United States Patent [19]

Hastings

[11] Patent Number: 5,775,338
[45] Date of Patent: Jul. 7, 1998

[54] HEATED PERFUSION BALLOON FOR REDUCTION OF RESTENOSIS

[75] Inventor: Roger N. Hastings, Maple Grove, Minn.

[73] Assignee: SciMed Life Systems, Inc., Maple Grove, Minn.

[21] Appl. No.: 781,663

[22] Filed: Jan. 10, 1997

[51] Int. Cl.$^6$ .................................................. A61B 19/00
[52] U.S. Cl. ........................... 128/898; 606/27; 604/113; 604/915; 607/113
[58] Field of Search ............................ 128/898; 606/7, 606/27-31, 113; 607/101, 98, 104, 122, 6, 96, 50, 62; 604/113, 915

[56] References Cited

U.S. PATENT DOCUMENTS

| | | |
|---|---|---|
| 4,643,186 | 2/1987 | Rosen et al. . |
| 4,662,368 | 5/1987 | Hussein et al. ............... 606/15 |
| 4,672,962 | 6/1987 | Hershenson . |
| 4,754,752 | 7/1988 | Ginsburg et al. .............. 606/27 |
| 4,773,413 | 9/1988 | Hussein et al. ............... 606/7 |
| 4,799,479 | 1/1989 | Spears .......................... 606/28 |
| 4,976,711 | 12/1990 | Parins et al. . |
| 5,019,075 | 5/1991 | Spears .......................... 606/7 |
| 5,035,694 | 7/1991 | Kasprzyk et al. . |
| 5,053,033 | 10/1991 | Clarke .......................... 606/3 |
| 5,106,360 | 4/1992 | Ishiwara et al. ............... 600/2 |
| 5,368,591 | 11/1994 | Lennox et al. . |
| 5,417,689 | 5/1995 | Fine ............................. 606/41 |
| 5,496,311 | 3/1996 | Abele et al. .................. 606/28 |

OTHER PUBLICATIONS

Sinclair et al. "Laser balloon angioplasty." Aust N Z J Med 17(4 suppl 2):571, Aug. 1987.
Wollenek et al. "Comparative study of different laser systems with special regard to agioplasty." THorac cardiovasc surg 36:126–132, 1988.

Lee et al. "Thermal compression and molding of atherosclerotic vascular tissue with use of radiofrequency energy." JACC 13(5):1167–75, Apr. 1989.

Zehler et al. "Radiofrequency 'hot balloon' angioplasty." Circ 80(4 suppl 2):ii255, 1989.

S. Black et al., "Heat Shock Proteins and the Ischemic Heart", Editorial Comment, Department of Pharmacology, University of Michigan Medical School, Ann Arbor, Michigan, Circulation vol. 87, No. 3, Mar. 1993, 4 pgs.

Publication entitled "Hot Rods Slow Tumor Growth", Technical Insights Alert, Bio/Med Technology Alert, Aug. 23, 1996, 1 pg.

*Primary Examiner*—Vincent Millin
*Assistant Examiner*—Kelly R. O'Hara
*Attorney, Agent, or Firm*—Nawrocki, Rooney & Sivertson

[57] ABSTRACT

A method for inhibiting the restenosis of blood vessel walls after angioplasty, including the application of low grade heat to the vessel walls. A heat applying perfusion catheter is advanced to a recently dilatated vessel region. Heat is applied to the region walls to inhibit restenosis. A preferred temperature range is from 42 to 45 degrees C. A preferred time period for treatment is from 3 to 6 minutes. A perfusion catheter allows longer heat treatment times. Electrical resistance heat, radio frequency current passage through inflation fluid, and microwave radiation are all heat sources within the scope of the invention.

6 Claims, 2 Drawing Sheets

HEATED PERFUSION BALLOON FOR REDUCTION OF RESTENOSIS

FIELD OF THE INVENTION

The invention relates generally to a method and apparatus for inhibiting restenosis in coronary arteries after angioplasty. More specifically, the invention includes using a heated perfusion catheter to apply low grade heat to a vessel wall for the purpose of inhibiting restenosis.

BACKGROUND OF THE INVENTION

Coronary arteries provide blood and nutrients to the heart muscle. The arteries are subject to atherosclerosis or hardening of the arteries. Vascular regions have plaques formed within, resulting in stenosed regions having reduced cross-sectional area. The reduced area causes a reduction in transport of blood, oxygen, and nutrients which can result in angina, myocardial infarction and death.

A commonly used method for treating atherosclerosis is Percutaneous Transluminal Coronary Angioplasty (PTCA). PTCA includes insertion of a balloon catheter through an insertion in the femoral artery near the groin, advancement of the balloon over the aortic arch, advancement within the selected coronary artery, continuing until the balloon portion is placed across the stenosed region. The balloon is inflated, widening the narrowed vessel region.

After catheter withdrawal, significant vessel reclosure may develop. The reclosure may occur within hours or days of dilation, an "abrupt reclosure." When reclosure does occur, it more commonly occurs progressively, within six months of the angioplasty. The gradual reclosure is referred to as "restenosis", and largely negates the dilatation treatment. More highly stenosed vessel regions have a greater chance of becoming restenosed.

One approach to dealing with restenosis utilizes stents, short tubular sections, placed across the recently dilatated vessel region. Stents can be either self-expanding or balloon-expandable. Stents are normally left in place indefinitely. As the stent is forever pushing radially outward against the vessel wall, the wall can be undesirably irritated over long time periods. Stent ends, which push radially outward, are adjacent to soft tissue which can be irritated by the stent end. Stents commonly have wire mesh or spring structures, with openings in the stent walls. "Intimal hyperplasia", rapid tissue growth through stent openings has also been reported. While the exact mechanism of restenosis is not understood, it is believed that the vessel narrowing is due more to cellular growth and/or a response to vessel injury than to an elastic rebound mechanism.

Thus, to prevent restenosis, use of a stent, or a stent without additional therapy, may not be a solution for all patients. An alternative to stents or an additional treatment associated with the use of stents may be desirably for some patients.

Once therapy for reducing restenosis which has been suggested is heated balloon angioplasty. Some attempts were directed to making the tissues "flow", by heating vessel tissue at 60 and 80 degrees C. Other attempts utilized high temperatures for the stated purpose of sealing the splitting of the intimal layers of the blood vessel walls, fusing tissue and coagulating. However, such attempts led to increased rather than decreased restenosis.

What is desirable and has not heretofore been provided is a method for inhibiting restenosis after a stent has been put in place. What would be more desirable is a method for inhibiting restenosis not requiring any stent placement.

SUMMARY OF THE INVENTION

The present invention is directed to a method and apparatus for inhibiting restenosis of blood vessels following angioplasty. In particular, the application of low grade heat to a recently dilatated stenosed vessel wall is believed to confer significant resistance to restenosis.

One method for practicing the invention includes heating a dilatated region vessel wall to a temperature within a 40 to 45 degree C. range for a period greater than 10 seconds. Preferred time periods can be greater than about 30 seconds, including the 30 second to 10 minute and 10 to 60 minute ranges. One preferred temperature range is from about 42 to about 45 degrees C. A preferred method includes heating a vessel wall to a temperature of 43 degrees C. for 3 to 6 minutes.

A preferred source of heat is a balloon catheter having a heating wire formed in a coil, with temperature sensors in the distal portion, electrically connected to a power supply and temperature display unit, respectively. A preferred catheter includes a wire coil which can be heated by the passage of DC, AC, or RF current through the coil. The coil in this embodiment is mounted on the outside wall of a perfusion tube and within a balloon cavity. Inflation fluid within the balloon cavity is in thermal contact with the wire and the balloon envelope is inflated to a low pressure in the range of 1 to 3 atmospheres to effect contact with the inner vessel wall, thereby providing thermal contact with the vessel wall. A heated coil thus provides heat to the vessel wall.

Accurate temperature measurement and control is one aspect of the present invention. Unlike previous heated angioplasty attempts, the purpose is not to fuse tissue but to apply controlled heat to a vessel region. While fusing tissue could be accomplished even without temperature measurement, low grade heat application requires tighter control. Specifically, the temperature should not exceed about 45 degrees C., to prevent cell necrosis. A preferred catheter includes a temperature sensor mounted along the balloon outside wall, for good contact with the vessel wall. A second, reference temperature sensor is optionally provided, measuring bloodstream temperature upstream of the heating device. An optional temperature measurement is a differential measurement of vessel wall temperature over blood temperature.

In another embodiment, radio-frequency (RF) current is supplied by the power supply to electrodes in the catheter head, causing current conduction through the inflation fluid, thereby heating the inflation fluid. In yet another embodiment, the wire in the catheter head is arranged in a configuration suitable for transmitting microwave radiation, including microwave radiation transmitted directly to vessel walls.

The invention provides low grade heat to inhibit restenosis in blood vessels. The variable power supplied, coupled with temperature feedback, provides a system for rapidly converging on proper operating parameters to achieve the desired vessel wall temperature. The perfusion lumen allows perfusing blood flow during the otherwise long treatment period. The invention can be used to treat a vessel region having a stent, to inhibit restenosis which may be caused in part by the stent placement.

DETAILED DESCRIPTION OF THE PREFERRED EMBODIMENTS

Figure 1:
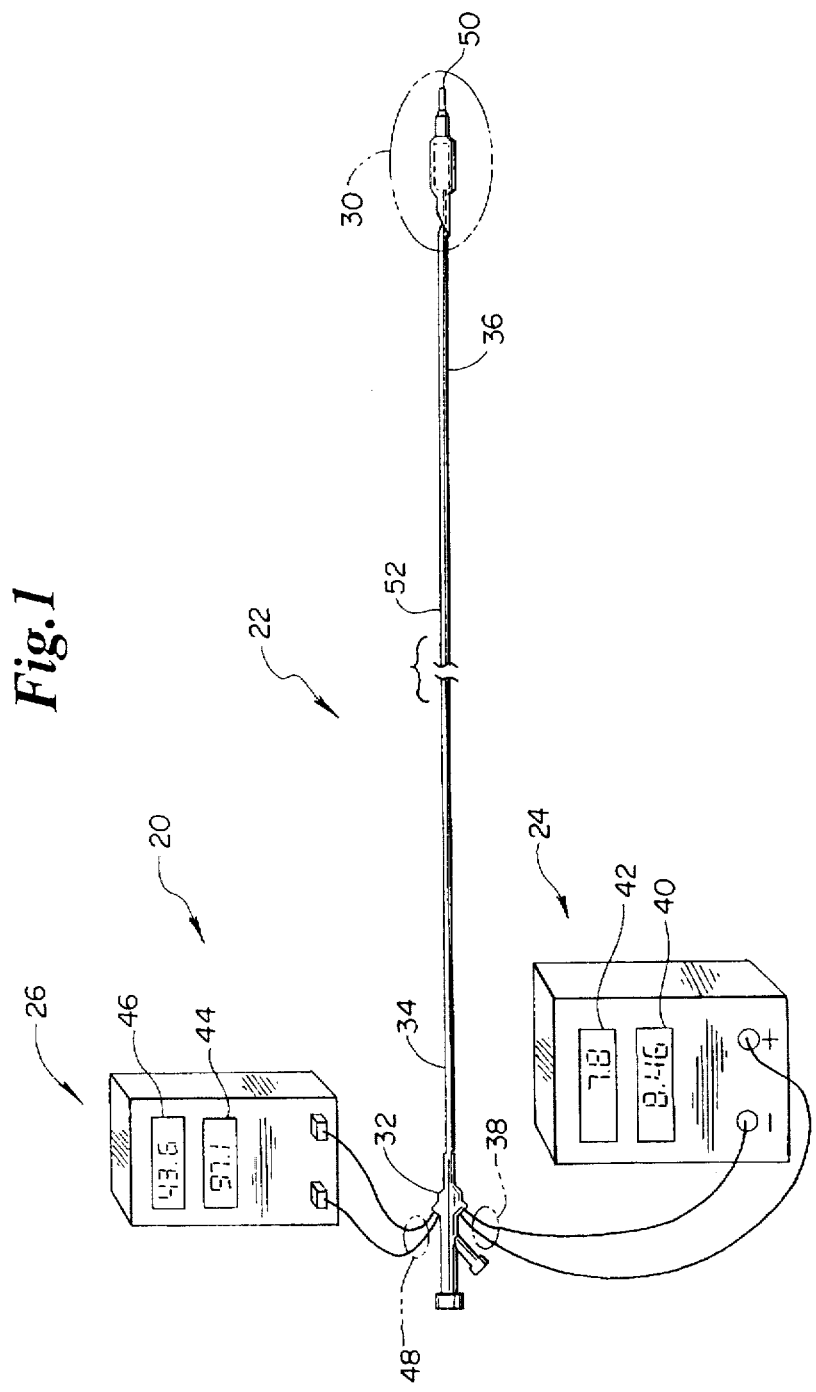
FIG. 1 is a diagrammatic view of a heat perfusion catheter system including current source and temperature display unit.

FIG. 1 illustrates, in a highly diagrammatic fashion, a system 20 for inhibiting restenosis including a catheter assembly 22, a power supply 24, and a temperature display unit 26. Catheter assembly 22 includes an elongate shaft 52 extending from a proximal portion 34 to a distal portion 36. A manifold 32 is operably attached to shaft proximal portion 34 and a heat perfusion head subassembly 30 is operably attached to shaft distal portion 36.

Power supply 24 can include a current display 40 and a voltage display 42. Supply 24 is electrically connected to catheter 22 with wire 38. Wire 38, in the embodiment illustrated in FIG. 1 is a two conductor wire. In one embodiment, supply 24 is a DC power supply. In another embodiment, supply 24 is an AC power supply. In yet another embodiment, supply 24 is a radio- frequency power supply. Supply 24 is adjustable, allowing power to catheter 22 to be adjusted to supply the desired current, frequency, and/or voltage, as displayed on displays 40 and 42.

Temperature display unit 26 includes a first temperature display 46. Display 46 shows a temperature indicating the temperature near the vessel walls being heated. In a preferred embodiment, this is obtained using a temperature sensor on a balloon surface. A preferred system includes a second temperature display 44 indicating a reference blood temperature. In one embodiment, this is obtained from a temperature sensor exposed to the bloodstream, upstream from the balloon. Temperature display unit 26 is electrically connected to catheter 22 with wire 48. Manifold 32 serves to introduce wires 38 and 48 into catheter 22, and to allow introduction of inflation fluid and guidewire, as will be appreciated by those skilled in the art.

Figure 2:
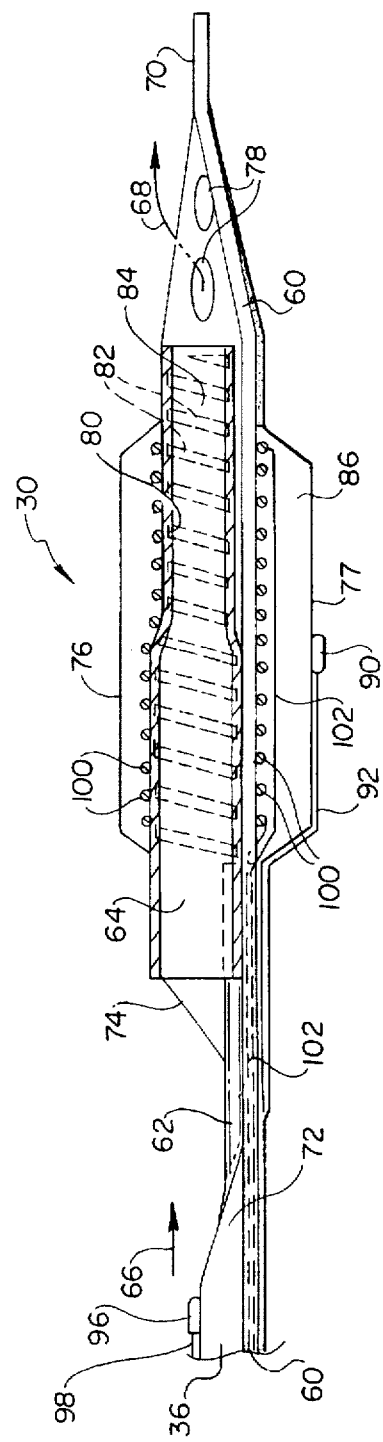
FIG. 2 is a fragmentary cross-sectional view of a heat perfusion catheter taken through a longitudinal axis.

FIG. 2 illustrates in greater detail heated perfusion head 30. A preferred embodiment includes a guidewire lumen 60, an inflation lumen 62, and a perfusion lumen 64. Perfusing blood flow is indicated by upstream arrow 66 and downstream arrow 68. Head 30 extends from shaft distal portion 36 to a projecting tip 70. Shaft 36 preferably skives down at 72, enhancing blood flow into blood inlet 74, through perfusion lumen 64, and out a series of discharge orifices 78. In a preferred embodiment, perfusion lumen 64 is defined by a tube 80. In one embodiment, tube 80 is formed of polyimide. A rigid tube 80 can serve to maintain a perfusion lumen against radial inward forces such as those generated by a balloon. In one embodiment, tube 80 is 2 cm in length and 1 mm in outside diameter. A preferred tube includes a helical member 82 supporting more flexible material 84 therebetween. The tube illustrated in FIG. 2 has a stepped-down geometry, providing a decreased profile for increased penetration into narrow vasculature.

Heated perfusion head 30 can contain a balloon 76 having an envelope 77 and an interior cavity 86. Inflation lumen 62 is in fluid communication with balloon interior cavity 86, allowing balloon inflation through injection of inflation fluid. Inflation lumen 62, in a preferred embodiment, contains guidewire lumen 60 within a guidewire tube.

Heated perfusion head 30 includes heating wire 100 located about tube 80. In a preferred embodiment, wire 100 is bonded to the outer surface of tube 80 with UV curable adhesive. In another embodiment, wire 100 is embedded within tube 80. In yet another embodiment, tube 80 includes an insulating layer. The insulating layer serves to lessen heat loss to the bloodstream within perfusion lumen 64. Wire 100 is electrically connected by supply wire 102, where wire 102 preferably has two conductors, a supply and return. As shown in FIG. 2, wire 102 can be run within inflation lumen 62, which in the embodiment of FIG. 2, contains guidewire lumen 60. Wires 102 may be simply an extension of coil wire 100.

Head 30 preferably also includes a first temperature sensor 90 and connecting wire 92, as well as a second, bloodstream temperature sensor 96 and connecting wire 98. In one embodiment, sensors 90 and 96 are optical and optical fibers serve to transmit temperature information. First temperature sensor 90 is preferably positioned on head 30 so as to come into close contact with the vessel wall. In one embodiment, temperature sensor 90 is a J-type thermocouple. In an embodiment having a balloon, sensor 90 is preferably positioned on the balloon envelope outer wall as indicated in FIG. 2. Bloodstream temperature sensor 96 is preferably located upstream of first temperature sensor 90. In a preferred embodiment, both sensors 90 and 96 are electrically connected to temperature display unit 26. In another embodiment, only the differential temperature information is transmitted to temperature display unit 26.

The present invention has a preferable range of about 42 to about 45 degrees C., or about 5 to 8 degrees C. above body temperature. This range is much less than the range in previous heated angioplasty attempts, where the stated purpose was to fuse tissues, coagulate blood, and seal the splitting of the intimal layers of the blood vessel wall. Previous heated angioplasty attempts could be practiced with little or no internal temperature measurements. The present invention requires tighter control.

For this reason, in one embodiment, the wall temperature is measured as a differential temperature over blood temperature. Any errors in measurement, such as miscalibration or unaccounted for resistance in thermocouple connecting wires, may be constant for both measurements, and not be reflected in a differential temperature reading. The differential reading can therefore be more accurate than comparing two separate readings. In one embodiment having a differential temperature measurement, only 1 pair of wires is required in the catheter.

In a preferred embodiment, power supply 24 supplies AC current to heating wire 100, where wire 100 is arranged in a coil upon tube 80 within balloon cavity 86. In one embodiment, the coil is formed of about 50 inches of 0.0018 inch diameter silver wire having H-ML polyimide insulation, supplied by California Fine Wire Co., Grover City Calif. In this embodiment, 0.0025 inch diameter silver wire having H-ML insulation is used for supply wire 102. In another embodiment, about 10 inches of 0.001 inch diameter platinum wire having H-ML insulation is used for heating wire 100. On one embodiment, the total resistance of heating wire 100 and supply 102 is 75 ohms. The electrical resistance provided by the wire generates heat in response to DC or AC current.

In use, after a stenosed region has been dilatated, the angioplasty catheter is withdrawn, leaving a guidewire in place. Heated perfusion catheter 22 then be threaded over the guidewire, and head 30 advanced to the widened region. Once in position, inflation fluid is injected into manifold 32, through inflation lumen 62, and into interior cavity 86 of balloon 76. Inflation continues until balloon 76 presses radially against the freshly dilated vessel inner walls. This presses temperature sensor 90 against the vessel walls, providing an initial reading of wall temperature. When present, bloodstream reference temperature sensor 96 provides the bloodstream temperature.

With temperature displayed on temperature display unit 26, power supply 24 is adjusted to provide initial voltage and current at a level previously indicated as within the range desired for bringing vessel walls to the desired temperature. Power supply 24 can be continually manually adjusted to bring about the desired vessel temperature displayed on unit 26. In one embodiment, about 200 milliamps at about 8 volts RMS into 75 ohms resistance is sufficient to bring about the desired heating.

Within balloon 76, heating wire 100 heats inflation fluid, which is in thermal communication with the balloon envelope which is in thermal communication with the vessel walls. Heated inflation fluid thus heats the interior vessel walls, with wall temperature being tracked on temperature display unit 26. In an alternate embodiment of the invention, wire 100 is brought into direct contact with the vessel interior walls. One such embodiment utilizes about 10 inches of 0.001 inch diameter platinum wire affixed to an balloon outer surface with UV curable adhesive (not shown). In yet another embodiment, resistive heating of the balloon envelope via a conductive polymer material or a conductive coating directly provides heat to the vessel interior walls.

The heat duration and temperature will vary depending upon the particular region to be treated and will be determined by the treating physician. One treatment elevates the vessel walls to a temperature in the range of 42 to 45 degrees C. for a period of at least 30 seconds. A preferred method heats the vessel walls for at least 5 minutes. Another preferred method heats vessel walls to 45 degrees C. for a period of between about 30 and 60 minutes. A preferred temperature is less than or equal to about 45 degrees C. The relatively long treatment time is enabled by the perfusive blood flow through the perfusion lumen. Once the heating is finished, power to head 30 is discontinued, the balloon can be deflated, and catheter 22 withdrawn from the patient.

In another embodiment, radio-frequency (RF) current is used to provide heat to the vessel walls. Lead wires 102 in this embodiment terminate on metal bands attached to the end of tube 80 at the distal and proximal ends of the balloon to allow current to pass through the inflation fluid within cavity 86. The current thus heats the fluid through conduction of RF current supplied by supply 24. In yet another embodiment, 100 is used as a microwave source to transmit microwaves within the vessel region, heating the vessel inner walls without necessarily requiring balloon 76 and the inflation fluid. The exact configuration of the microwave transmitting wire is determined by the power supplied and the transmitting power desired at catheter head 30. Microwave antennae design and the characteristics of absorbing materials are well known to those in the microwave art. It is not necessary to transmit an exact power level and utilize a precisely correct antennae design as supply 24 and temperature display 26 provide constant feedback and allow for rapid convergence on the optimal operating parameters in each case.

It will be appreciated that the vessel wall temperature can be obtained in a variety of ways, including inferring wall temperatures from sensors not directly contacting the vessel walls. Optimally, wall temperature can be measured or inferred from outside of the vessel. Providing closed loop control of the power using wall temperature feedback is within the scope of the invention.

EXPERIMENTAL RESULTS

A perfusion balloon catheter having a heating coil within the balloon cavity was created. A first lesion was created in a pig using 80 degree C. heat. A second lesion was created in the pig using a copper stent. Approximately one month later two highly significant lesions were present, which could not be crossed with the heated perfusion balloon. Both lesions were dilated with standard balloon catheters to leave patent lumens. The modified perfusion balloon was used to heat each lesion to an elevated temperature below 45 degrees for approximately five minutes at a pressure of approximately 2 atmospheres. The balloons were oversized (4 mm) to guarantee good contact of the balloon with the arterial wall. The animal was released.

Approximately one month later the arteries were examined. Both treated areas were patent under angiography. The fractional flow reserve was measured across each area, the value being 1.0 in both cases, indicating no significant blockage.

A large degree of restenosis was expected, the above results were unexpected. In particular, the animal was not expected to live. In particular, large blockages were anticipated. The heat treatment thus appeared to significantly inhibit restenosis following angioplasty. Applicants speculate that the unexpected results might be related to the release of heat shock proteins at approximately 43 degrees C.

Numerous and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method for inhibiting restenosis in a vessel region comprising the steps of:

heating said vessel region at a temperature in the range of about 40 degrees C. to about 45 degrees C. for a time period of 10 seconds to 60 minutes.

2. A method for inhibiting restonosis as recited in claim 1, wherein said temperature is within the range of about 42 degrees to about 45 degrees C.

3. A method for inhibiting restonosis as recited in claim 1, wherein said time period is within the range from about 30 seconds to about 10 minutes.

4. A method for inhibiting restonosis as recited in claim 1, wherein said time period is within the range from about 10 minutes to about 60 minutes.

5. A method as recited in claim 1, wherein said heating is produced using a heat source selected from the group consisting of electric resistance, radio-frequency current passage through fluid, and microwave radiation.

6. A method as recited in claim 1, further comprising the step of measuring blood temperature within the vessel and measuring the vessel wall temperature.

* * * * *